United States Patent [19]

Stearns

[11] 4,173,363
[45] Nov. 6, 1979

[54] ADAPTOR ASSEMBLY FOR FITTINGS AND CONNECTIVE LINES OF DIFFERING SIZES

[76] Inventor: Stanley D. Stearns, 1201 Archley Dr., Houston, Tex. 77055

[21] Appl. No.: 921,167

[22] Filed: Jul. 3, 1978

[51] Int. Cl.² ............................................ F16L 55/00
[52] U.S. Cl. ...................................... 285/177; 285/18
[58] Field of Search .................. 285/18, 39, 138, 176, 285/177, 370, 397, 417

[56] References Cited

U.S. PATENT DOCUMENTS

| | | | |
|---|---|---|---|
| 582,137 | 5/1897 | Dockery | 285/177 X |
| 1,665,346 | 4/1928 | Clarke | 285/177 |
| 2,562,294 | 7/1951 | Cahenzli, Jr. | 285/177 |
| 2,702,201 | 2/1955 | Romanelli et al. | 285/39 X |
| 3,255,521 | 6/1966 | Callahan, Jr. | 285/18 X |
| 3,977,702 | 8/1976 | White et al. | 285/18 |

FOREIGN PATENT DOCUMENTS 1027853 2/1953 France ...................... 285/138

Primary Examiner—Mervin Stein
Assistant Examiner—Carl Pietruszka
Attorney, Agent, or Firm—Donald Gunn

[57] ABSTRACT

An adaptor assembly is disclosed in two embodiments. Each embodiment is for connecting a tubing to a fitting of different size. The alternate embodiment is similar to the first embodiment except that it cooperates with a male fitting as opposed to a female fitting. In the embodiment for connection to a female fitting, a hollow threaded nut drives a tapered spool into a tubular seat, and the tubing is placed on the interior of the nut, spool and seat. All of this is placed in a hollow threaded adaptor which abuts a larger tapered spool, all of which threads into the female fitting. When the components are threaded together, they squeeze and clamp the tubing. The tubing, once clamped, is held securely and cannot be pulled free. The threaded adaptor has a wall thickness enabling it to mate with a fitting of any suitable size. The male counterpart equipment is similar in construction except that the adaptor coupling is provided with two sets of threads arranged respectively at countersunk internal axial portions to receive a male fitting thereinto.

10 Claims, 4 Drawing Figures

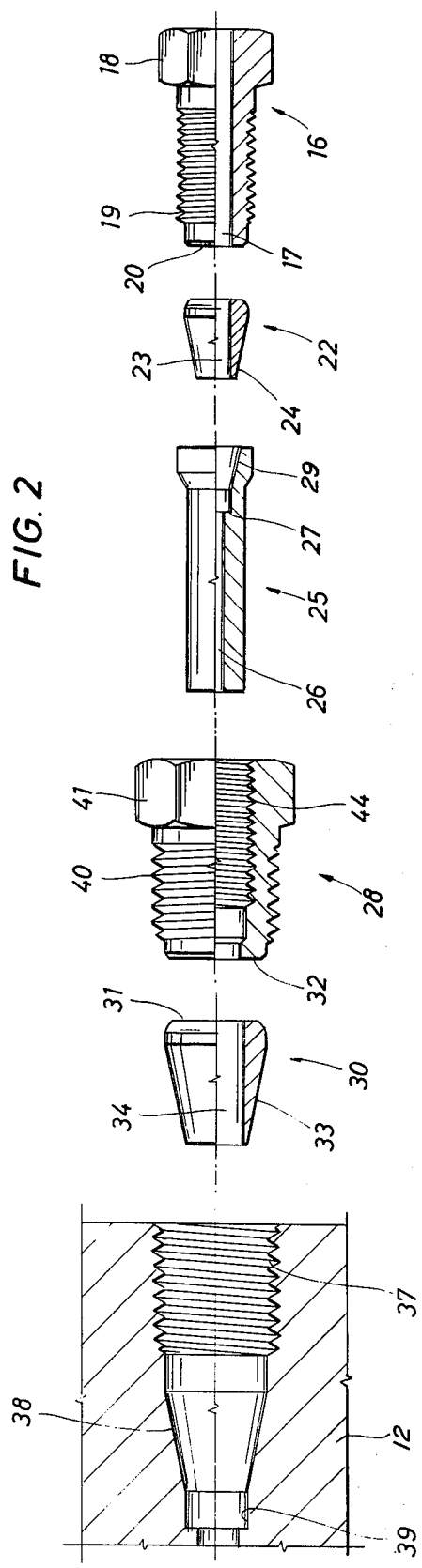
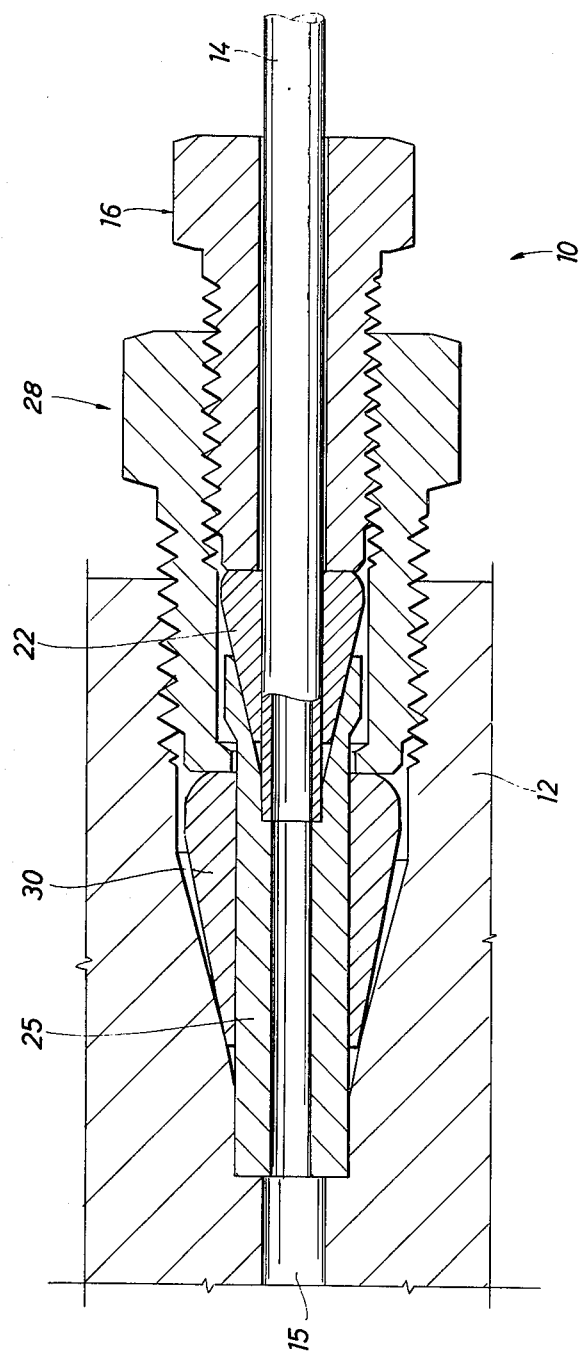
FIG. 2
FIG. 1

ADAPTOR ASSEMBLY FOR FITTINGS AND CONNECTIVE LINES OF DIFFERING SIZES

BACKGROUND OF THE PROBLEM

In the assembly of laboratory test equipment, it is often necessary to connect a sample line into test equipment such as a valve, test instruments and the like. These are manufactured by many different makers, and, quite often, they are constructed in accordance with differing standards, or indeed, no particular standard whatsoever with regard to the size of the fittings. For instance, it is often necessary to connect lines as small as one sixteenth of an inch OD into a fitting which is perhaps as large as one quarter inch or even five sixteenths of an inch. Sometimes, it is necessary to connect fittings which differ only by one sixteenth of an inch. Even so, all such mismatched connections are difficult without regard to how different the respective measures of the misfit might be.

Typical laboratory test equipment including test instruments, valves and the like generally are manufactured with a common thread standard. However, there is no standard as to the diameter of the fittings. Sometimes it will be necessary to connect into a female internally tapped opening of a test instrument. At other times, the test instrument may incorporate a threaded male fitting. The present invention is an apparatus which cooperates with an internally tapped female fitting or an externally threaded male fitting. In particular, it enables connection of a misfitted arrangement. By misfitted. reference is made to connection of a tubing to a fitting where the tubing is different in size from the fitting. This is normally intended for use in laboratory and test instruments where typical sizes are in the range of about one sixteenth of an inch OD to not more than one-half inch. Within the range of these typical sizes, tubing which is typically formed of copper or some plastic material (e.g., polyethylene) with adequate wall thickness to provide suitable strength against the crushing force is used.

The present apparatus is further advantageous in that the equipment is assembled quite easily. It is assembled by threading members together into the fitting. They are assembled to it sequentially. This more readily permits one-handed assembly as opposed to requiring two wrenches held in two hands. While there are many components which require wrench tightening, they are, nevertheless, assembled at different times, and, therefore, they are conveniently assembled by the use of only a single wrench.

The term "fitting" which is used herein refers to a male or female fitting which is typically an input for a test instrument or larger instrument. By way of example and not limitation, it may be a multiport valve assembly, a chromatographic analyzer and so on.

BRIEF SUMMARY OF THE PRESENT DISCLOSURE

This disclosure is directed to an adaptor assembly for connection to a fitting where there is a mismatch in size between a tubing to be connected to the fitting and the fitting itself. The adaptor is particularly able to be placed and held on the end of a tubing by clamping action. When clamped, it enables the tubing to be communicated into the fitting. It incorporates a hollow threaded nut which slides loosely around the tubing and which is positioned adjacent to a tapered spool. This is arranged serially with an elongate hollow sleeve which is received into a coupling. At this juncture, differences between male and female versions must be noted. For a female fitting, the coupling is internally and externally threaded. For a male fitting, the coupling is axially threaded with two different sets of threads formed in it which are located at opposite ends and which have differing diameters. The coupling jams a second tapered spool into or against the fitting. When assembled, the end of the tube is externally gripped with a force applied by the tapered member which surrounds it. The two tapered spools abut corresponding tapered surfaces which give rise to a wedging action when the members are screwed together.

BRIEF DESCRIPTION OF THE DRAWINGS

FIG. 1 is a sectional view of the present invention installed in a female fitting and clamping a tube in axial communication with a mismatched opening in the fittings;

FIG. 2 is an exploded view showing the parts of the apparatus in exploded view, partly in section;

DETAILED DESCRIPTION OF THE PREFERRED EMBODIMENTS

Figure 4:
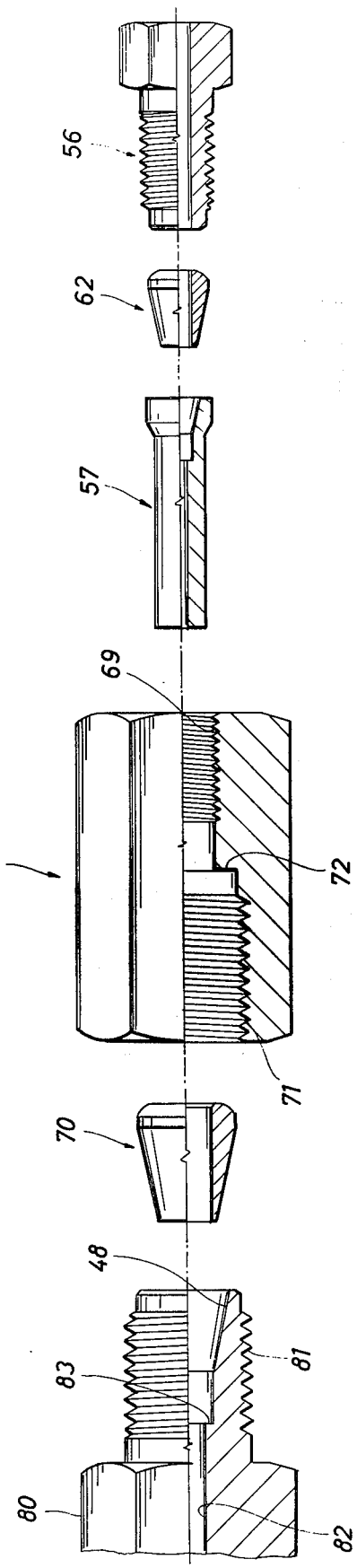
FIG. 4 is an exploded view of the apparatus shown in FIG. 3 where the parts are shown in sectional view.
Figure 3:
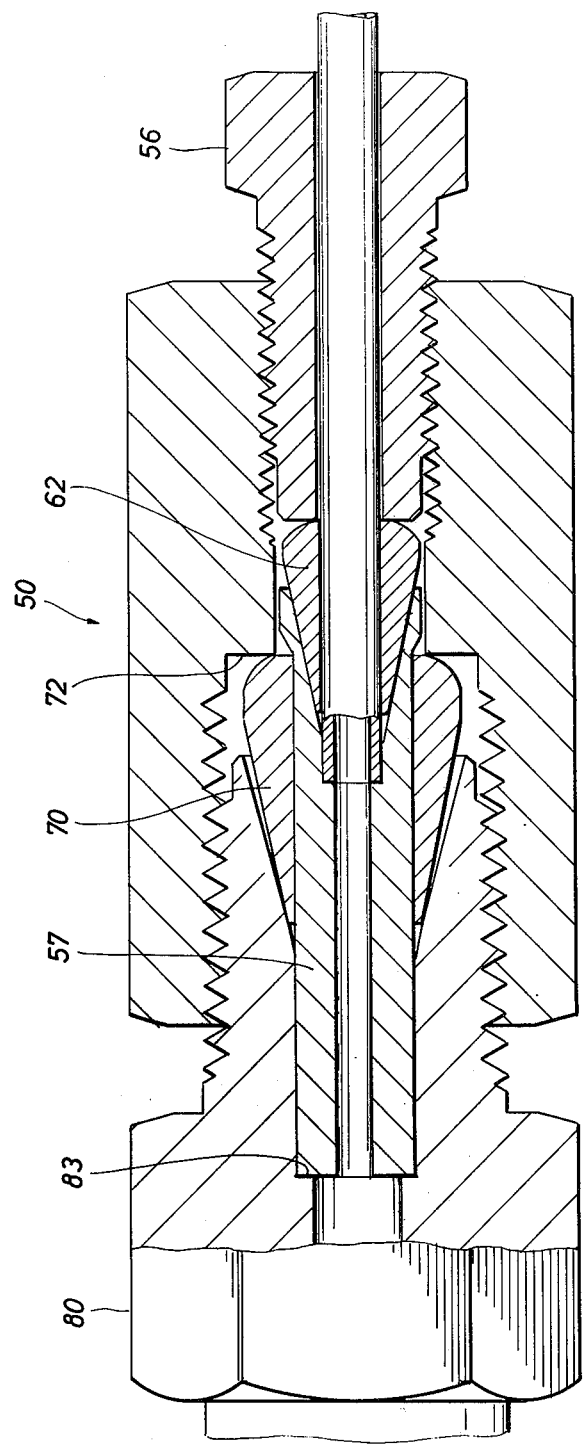
FIG. 3 is a sectional view through the present invention installed on a male fitting.

In FIG. 1 of the drawings, the adaptor of the present invention is identified generally by the numeral 10 and is shown installed in a fitting 12. It connects a tubing 14 to the fitting 12. The fitting 12 is an internally threaded tapped opening at the end of a passage 15. The passage 15 is different in diameter from the ID of the tubing 14. The adaptor of the present invention finds its best use and application in connecting mismatched conduits such as the tube 14 with the passage 15. The fitting 12 is a body having a size which is subject to variation; it can be small or large as needed. In particular, it is constructed with an internally threaded opening at the end of the passage 15. It is formed in a metal body typically, and the metal body is large or small, and is normally a constituent of or an accessory to a laboratory test instrument. It is not profitable to exhaust the list of test instruments which use tubing connections in the range of about one sixteenth OD tubing up to about one-half inch or so. In any case, the fitting 12 defines equipment which is cooperative with the present invention.

In FIG. 2 of the drawings, the numeral 16 identifies a hollow threaded nut. It includes an internal passage 17 which is sized to fit loosely around the tubing 14. The hollow nut has wrench flats 18 at the head and a generally hollow cylindrical elongate body. Threads are formed on the exterior at 19, and the nut terminates at a generally flat transverse face 20.

The face 20 abuts the end of a tapered spool 22. The spool 22 is axially hollow at 23 and is sized so that the tubing 14 fits loosely in it. It has an external face 24 which is tapered. It is provided with adequate wall thickness so that it does not collapse under radial loading.

The tapered spool 22 is radially loaded and therefore is able to grip the tubing 14 when it is assembled with the remaining components.

The numeral 25 identifies an elongate hollow tubular member. It is constructed with an axial passage at 26 which is smaller than the OD of the tubing 14. The tubing 14 is inserted until it comes to rest against a shoulder 27. The end of the rather long component 25 is counterbored to define a step radius adjacent to the shoulder 27 and the counterbore is flared at 2a to define a tapered internal surface coacting with the tapered external surface on the tapered spool 22.

The elongate hollow sleeve 25 passes all of the way through a coupling 28 and through a larger tapered spool 30. The spool 30 incorporates an end face 31 which abuts against an end face 32 on the coupling. It has a tapered external face 33 and an axial passage 34 which is larger than the sleeve 25. Thus, the sleeve 25 fits inside of both the coupling and the tapered spool.

The fitting 12 is internally threaded at 37 and has a tapered surface 38 which mates with and contacts against the external tapered surface on the spool 30. The sleeve 25 fits in the fitting 12 and abuts a shoulder 39 which defines the end of the countersunk portion of the fitting at the passage 15.

The threads 37 engage matching threads at 40 formed on the coupling 28. The threads 40 are found on the exterior, and an enlargement is immediately adjacent thereto which is provided with wrench flats 41. The wrench flats 41 enable the coupling 28 to be threaded into the fitting 12 until the tapered spool 30 limits its penetration. The elongate sleeve bottoms out against the shoulder 39. The elongate sleeve is not held by the coupling as such, but it is jammed home when the nut 16 is threaded to the coupling 28. To this end, the coupling is internally threaded at 44 with a set of threads on the interior for engaging the threads 19 on the nut 16. The coupling thus adapts a smaller size to a larger size, and to this end, the coupling 28 is formed with different wall thicknesses. This accommodates the mismatch in the tubing to be connected to the fitting.

Considering now the manner in which the device is assembled, the nut 16 is placed on the end of a tubing and is slid up the tubing. The tapered spool 22 is next placed on the tubing and is also moved up the tube. The tubing is then loosely inserted into the elongate sleeve 25 until it bottoms out against the shoulder 27. It is preferable to trim the end of the tubing so that it is reasonably square. At this juncture, the coupling 28 is positioned or telescoped around the sleeve 25 and moved to the left so that the sleeve protrudes from the end of it. The spool 30 is next positioned around the sleeve 25. The coupling 28 and the hollow tapered spool are then positioned adjacent to the fitting 12. Using finger tightening techniques, the coupling 44 is loosely threaded into the threads 37 to drive home the tapered wedge 30. The sleeve 25 is pushed into the fitting until it bottoms out against the shoulder 39. At this juncture, the nut 16 is also tightened finger tight into the coupling 28.

The coupling 28 is then tightened snuggly with a wrench, and thereafter, the nut 16 is tightened into the coupling with a wrench. When the coupling 28 is tightened into the fitting, it jams the tapered spool and forces it radially inwardly to grip the sleeve 25. This holds the sleeve 25 securely in position against slippage. When the nut 16 is tightened into the coupling 28, it jams the tapered spool 22 into the sleeve 25. This causes it to grip the tubing 14 firmly. Slippage is prevented, and the tubing is held in position. FIG. 1 shows the end of the sleeve 25 flaring somewhat when the tapered spool 22 is forced into it. This aids in gripping and holding all of the equipment together. This enables the tubing to be held firmly against pulling free from the fitting.

The degree of mismatch is typically not more than perhaps three sixteenths or four sixteenths of an inch. This is accommodated in the wall thickness of the sleeve 25 and the coupling 28. Needless to say, the axial passage formed in the threaded nut 16, the tapered spool 22 and the sleeve 25 can be varied; this variation, of course, accomodates variations in wall thickness of the tubing itself and the degree of mismatch.

It will be observed that the line 14 cannot slip. The line 14 is held by axial thrust of the tapered spool 22. It does not slip or rotate because it has a substantial and significant frictional engagement with the tapered surface 28 in the elongate sleeve 25.

Going now to the alternate embodiment which is identified by the numeral 50, it is shown in FIG. 4 of the drawings to incorporate a hollow nut 56. The hollow nut is similar or even identical to the nut 16 shown in FIG. 2. It fits adjacent to a tapered spool 62 which is similar to or even identical to the spool 22 shown in FIG. 2, again presuming installation on identical sizes of tubing. The elongate sleeve 57 is similar to or identical to the sleeve 25 shown in FIG. 2. The components 56, 62 and 57 are assembled to the tubing in the same manner and sequence.

The coupling 68 is different from the coupling 28. The coupling 28 has a specified wall thickness between concentric sets of threads, one on the interior and one on the exterior. The coupling 68 is provided with an internal set of threads 69 and a second, larger set of threads 71. They are serially arranged in the internal axial passage. The threads 69 match the threads on the hollow threaded nut 56. The threads 70 match the external threads 81 of a male fitting 80. The male fitting 80 is externally threaded at 81. The threads 81 mate with the threads at 71. The threads 69 and 71, which are formed on the interior of the coupling 69, define an internal shoulder 72 having a width dependent on the measure of mismatch. For a significant mismatch, the shoulder 72 is quite large. The shoulder 72 limits the axial penetration of a tapered spool 70 into the coupling 68. The tapered spool 70 is similar to or even identical to the tapered spool 30 shown in FIG. 2, again presuming fairly similar dimensions for the tubing and the fitting.

The male fitting 80 is equipped with the external threads 81. It has an internal passage 82 of some selected diameter. It terminates at a shoulder 83 which limits entry of the sleeve 57. The fitting is chambered with a tapered surface 48, having an angle which approximately matches the tapered spool 70.

Assembly of the components occurs in the following manner. The hollow nut 56 and the tapered spool 62 are threaded around the tubing and pushed to the left. The tubing is jammed into the sleeve 57 and seated against the internal shoulder.

After the sleeve 57 is temporarily mated with the tubing, the sleeve 57 is threaded through the coupling 68 very loosely and through the tapered spool 70. The sleeve 75 is forced against the shoulder 83, and the tapered spool 70 is positioned against the tapered surface 48 of the fitting 80. The coupling 68 is threaded finger tight to the fitting 80. The threaded nut 56 is then threaded into the coupling 68 at the threads 69. Thereafter, a wrench is used to tighten the coupling 68 which jams the tapered spool 70 home against the sleeve 57 which cannot thereafter escape. The wrench is then used to tighten the threaded nut 56. It grips the tubing by the wedging action of the spool 62 in conjunction with the elongate sleeve 57. This holds the entire assembly to the fitting and, in turn, holds the tubing in the assembly, thereby completing the connection. As will be understood, the degree of mismatch is accommodated quite easily in the coupling 68 by altering the relative dimensions of it.

Disassembly of both devices is achieved by simply removing the threaded nut from the end of the assembly and thereafter, unthreading the coupling. This is achieved rather quickly and can be accomplished with a single wrench.

The foregoing is directed to the preferred embodiments. Representative sizes have been given. Suitable materials are brass and stainless steel. For less critical applications, fairly high density plastics can be used. When the device is assembled or disassembled, the parts can be used over many times. The foregoing is directed to the preferred embodiments, but the scope is determined by the claims which follow.

I claim:

1. An adaptor for connecting a tubing to a fitting to accommodate a mismatch in size, comprising:
   (a) a hollow nut adapted to be positioned around a tubing;
   (b) an elongate hollow tubular sleeve having an internal shoulder facing the end of the tubing;
   (c) a first tapered spool adapted to be forced into the end of said sleeve by said nut and surrounding said tubing to wedge against the tubing and thereby grip around it;
   (d) an elongate coupling having
      (1) an axial passage therethrough;
      (2) a first set of threads at one end of said passage for engaging said hollow nut;
      (3) a second set of threads concentric with said first set for connection to a fitting;
      (4) a shoulder facing away from the end at which said hollow nut is threaded to said coupling; and
      (5) a radial thickness in said coupling defined between the radii of said first and second sets of threads which is at least in part related to the difference in diameter between the tubing and fitting; and
   (e) a second and larger tapered spool adapted to be abutted against said shoulder and inserted into a tapered seat in the fitting surrounding said hollow sleeve and wedging against it to grip it in axial communication with a passage in the fitting.

2. The apparatus of claim 1 wherein said nut is constructed and arranged with an end located exposed face for abutting said first tapered spool; and an elongate barrel extending from said face to an enlarged head having tool engaging means thereon and wherein said elongate barrel is threaded to match said first set of threads.

3. The apparatus of claim 1 wherein said first tapered spool includes an axial passage sized to fit around the tubing and has an exterior which tapers to a narrow end from a larger end and wherein the tapered face is constructed and arranged to fit into an internal and complementary tapered seat within said coupling.

4. The apparatus of claim 1 wherein said second tapered spool includes an axial passage sized to fit around said sleeve and has an exterior which tapers to a narrow end from a larger end and wherein the tapered face is constructed and arranged to fit into an internal and complementary tapered seat within and centered in the fitting to grip said sleeve.

5. The apparatus of claim 1 wherein said sleeve includes a tapered internal axial opening at the end thereof adjacent to said internal shoulder and wherein said tapered opening limits entry of said first tapered spool thereinto.

6. The apparatus of claim 1
   (a) wherein said nut is constructed and arranged with an end-located exposed face for abutting said first tapered spool; an elongated barrel extending from said face to an enlarged head having tool engaging means thereon and wherein said elongated barrel is threaded to match said first set of threads;
   (b) wherein said first tapered spool includes an axial passage sized to fit around the tubing and has an exterior which tapers to a narrow end from a larger end and wherein the tapered face is constructed and arranged to fit into an internal and complementary tapered seat within said coupling;
   (c) wherein said second tapered spool includes an axial passage sized to fit around said sleeve, and has an exterior which tapers to a narrow end from a larger end and wherein the tapered face is constructed and arranged to fit into an internal and complementary tapered seat within and centered in the fitting to grip said sleeve; and
   (d) wherein said sleeve includes a tapered internal axial opening at the end thereof adjacent to said internal shoulder and wherein said tapered opening limits entry of said first tapered spool thereinto.

7. The apparatus of claim 1 wherein said coupling has said first set of threads on the interior thereof and said second set of threads is on the exterior thereof for fitting into a female fitting which fitting includes internal threads mating with said second set of threads, and said coupling terminates at one end in an enlarged head having tool engaging means thereon for ease of threading said coupling to the female fitting.

8. The apparatus of claim 1 wherein said coupling has said first set of threads formed internally at end of the axial passage therethrough, and said second set of threads is formed internally at the other end thereof for fitting around a male fitting having an external set of threads, and said shoulder is on the interior between said first and second sets of threads and said axial passage is sufficiently large to encircle and enclose said second spool and the end of the male fitting, and said coupling incorporates an external surface having an exposed tool engaging means thereon for ease of threading said coupling to the male fitting.

9. The apparatus of claim 7 wherein
   (a) said nut is constructed and arranged with an end-located exposed face for abutting said first tapered spool; an elongate barrel extending from said face to an enlarged head having tool engaging means thereon and wherein said elongate barrel is threaded to match said first of threads;
   (b) said first tapered spool includes an axial passage sized to fit around the tubing and has an exterior which tapers to a narrow end from a larger end and wherein the tapered face is constructed and arranged to fit into an internal and complementary tapered seat within said coupling;
   (c) said second tapered spool includes an axial passage sized to fit around said sleeve, and has an exterior which tapers to a narrow end from a larger end and wherein the tapered face is constructed and arranged to fit into an internal and complementary tapered seat within and centered in the fitting to grip said sleeve; and (d) said sleeve includes a tapered internal axial opening at the end thereof adjacent to said internal shoulder and wherein said tapered opening limits entry of said first tapered spool thereinto.

10. The apparatus of claim 8 wherein (a) said nut is constructed and arranged with an end-located exposed face for abutting said first tapered spool; an elongate barrel extending from said face to an enlarged head having tool engaging means thereon and wherein said elongate barrel is threaded to match said first of threads;

(b) said first tapered spool includes an axial passage sized to fit around the tubing and has an exterior which tapers to a narrow end from a larger end and wherein the tapered face is constructed and arranged to fit into an internal and complementary tappered seat within said coupling;

(c) said second tapered spool includes an axial passage sized to fit around said sleeve, and has an exterior which tapers to a narrow end from a larger end and wherein the tapered face is constructed and arranged to fit into an internal and complementary tapered seat within and centered in the fitting to grip said sleeve; and (d) said sleeve includes a tapered internal axial opening at the end thereof adjacent to said internal shoulder and wherein said tapered opening limits entry of said first tapered spool thereinto.

* * * * *